(12) United States Patent  
Moraviec

(10) Patent No.: US 9,639,953 B2  
(45) Date of Patent: May 2, 2017

(54) SURGICAL MECHANISM CONTROL SYSTEM

(71) Applicant: Freehand 2010 Ltd, Guildford, Surrey (GB)

(72) Inventor: Paul Moraviec, Bracknell (GB)

(73) Assignee: Freehand 2010 Ltd, Guildford (GB)

( * ) Notice: Subject to any disclaimer, the term of this patent is extended or adjusted under 35 U.S.C. 154(b) by 0 days.

(21) Appl. No.: 14/927,322

(22) Filed: Oct. 29, 2015

(65) Prior Publication Data

US 2016/0045274 A1    Feb. 18, 2016

Related U.S. Application Data

(63) Continuation of application No. 12/565,690, filed on Sep. 23, 2009, now Pat. No. 9,176,580.

(30) Foreign Application Priority Data

Sep. 25, 2008  (GB) .................................. 0817502.8

(51) Int. Cl.  
*G06F 3/01* (2006.01)  
*G06T 7/20* (2017.01)  
(Continued)

(52) U.S. Cl.  
CPC ........ G06T 7/2033 (2013.01); A61B 19/2203 (2013.01); A61B 19/5244 (2013.01);  
(Continued)

(58) Field of Classification Search  
CPC .................. G06F 3/012; G06T 7/2033; G06T 2207/10016; G06T 2207/30204; G06T 7/00; G06T 11/00; G06T 19/006; A61B 19/2203; A61B 19/5244; A61B 2034/2048; A61B 2034/302; G02B 27/0093; G02B 27/01; H04N 13/0468  
See application file for complete search history.

(56) References Cited

U.S. PATENT DOCUMENTS 4,150,285 A   4/1979  Brienza et al.  
4,601,206 A * 7/1986  Watson ................. G01C 21/16  
                                                      73/510

(Continued)

FOREIGN PATENT DOCUMENTS

EP          0836150          1/2002  
NL   WO 2006025732 A3 * 11/2006 ............ G06F 3/012  
WO       2006/087689         8/2006

*Primary Examiner* — Stephen Holwerda  
(74) *Attorney, Agent, or Firm* — Lewis, Reese & Nesmith, PLLC

(57) ABSTRACT

A surgical mechanism control system including an acceleration or orientation detection unit to output a control signal in response to detecting an acceleration or orientation of the unit, the unit being attachable to a surgeon. The unit includes an acceleration sensor and the acceleration sensor has an associated threshold acceleration, such that an acceleration below the associated threshold acceleration does not cause actuation of an associated switch unit and an acceleration above the associated threshold acceleration does cause the associated switch unit to actuate. A control signal is output on actuation of the switch unit and foot pedal, and the control signal is used to control a surgical mechanism.

13 Claims, 12 Drawing Sheets

(51) Int. Cl.
*A61B 19/00* (2006.01)
*A61B 34/37* (2016.01)
*A61B 34/30* (2016.01)
*A61B 34/20* (2016.01)
*A61B 90/00* (2016.01)

(52) U.S. Cl.
CPC .............. *A61B 34/37* (2016.02); *G06F 3/012* (2013.01); *A61B 2034/2048* (2016.02); *A61B 2034/302* (2016.02); *A61B 2090/372* (2016.02); *G06T 2207/10016* (2013.01); *G06T 2207/30204* (2013.01)

(56) References Cited

U.S. PATENT DOCUMENTS

| | | | |
|---|---|---|---|
| 4,713,535 A | 12/1987 | Rhoades | |
| 4,988,981 A | 1/1991 | Zimmerman et al. | |
| 5,091,926 A | 2/1992 | Horton et al. | |
| 5,345,087 A | 9/1994 | Luber et al. | |
| 5,383,454 A | 1/1995 | Bucholz | |
| 5,436,542 A * | 7/1995 | Petelin | B25J 9/1679 318/567 |
| 5,558,619 A | 9/1996 | Kami et al. | |
| 5,645,077 A * | 7/1997 | Foxlin | A61B 5/1114 600/587 |
| 5,828,447 A | 10/1998 | Duchon et al. | |
| 5,876,325 A | 3/1999 | Mizuno et al. | |
| 5,907,664 A * | 5/1999 | Wang | B60R 21/0132 600/101 |
| 5,987,349 A | 11/1999 | Schulz | |
| 6,239,874 B1 | 5/2001 | Harwood | |
| 6,714,841 B1 | 3/2004 | Wright et al. | |
| 7,599,044 B2 | 10/2009 | Hotelling et al. | |
| 7,835,498 B2 | 11/2010 | Bonfiglio et al. | |
| 7,851,736 B2 | 12/2010 | Spahn | |
| 8,174,358 B2 | 5/2012 | Butzine et al. | |
| 2003/0002033 A1 | 1/2003 | Boman | |
| 2006/0064121 A1* | 3/2006 | Sempe | A61F 9/0133 606/166 |
| 2008/0030467 A1* | 2/2008 | Doornekamp | G06F 3/012 345/158 |
| 2008/0136916 A1 | 6/2008 | Wolff | |
| 2008/0211768 A1* | 9/2008 | Breen | G06F 3/012 345/157 |
| 2008/0253519 A1* | 10/2008 | Bonfiglio | A61B 6/00 378/65 |

\* cited by examiner

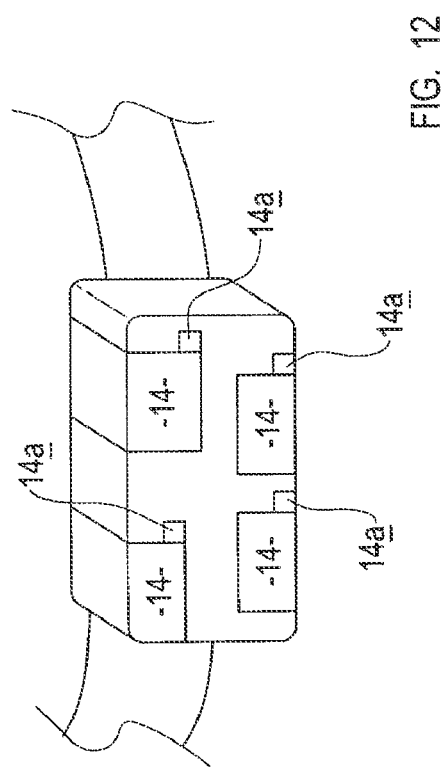

SURGICAL MECHANISM CONTROL SYSTEM

CROSS-REFERENCE TO RELATED APPLICATIONS

This application is a continuation of U.S. Non-Provisional patent application Ser. No. 12/565,690, filed Sep. 23, 2009 (allowed), which claims priority to GB 0817502.8, filed on Sep. 25, 2008, which is incorporated herein by reference in its entirety.

BACKGROUND AND SUMMARY OF THE INVENTION

The present invention relates to a surgical mechanism control system. Specifically, embodiments of the present invention include to an orientation detection arrangement for detecting the orientation of a surgeon's head and using that information to control a surgical mechanism. Embodiments of the present invention include a surgical mechanism control system and a surgical laparoscope positioning arrangement.

Minimally invasive surgery is preferred over traditional surgical methods because of improved recovery times and reduced risks of infection. Endoscopic surgery is a form of minimally invasive surgery and laparoscopic surgery is a sub-category of endoscopic surgery which is specifically concerned with abdominal endoscopic surgery.

During endoscopic surgery, a surgical assistant is normally required to hold an endoscope in the desired position while the surgeon uses one or more endoscopic surgical tools to perform the surgical operation. An image captured from a distal end of the endoscope (i.e. the end of the endoscope which is located inside the patient and substantially at the surgical site) is displayed for the surgeon's use on a monitor in the operating theatre. An endoscopic surgical operation can take several hours and the surgical assistant must hold the endoscope in the position desired by the surgeon for the duration of the operation (making any position adjustments under instructions from the surgeon).

More recently, surgical mechanisms and robots have been developed which can hold the endoscope in the desired position and which can automatically move the position of the endoscope in accordance with instructions from the surgeon.

It is difficult for the instructions of the surgeon to be passed directly to the surgical mechanism or robot because the surgeon is often using both of his hands to control the endoscopic surgical tools and, in any event, the surgeon must keep his hands sterile (and hence cannot touch any non-sterile control mechanism).

An orientation detection arrangement has been proposed in, for example, U.S. Pat. No. 6,239,874, which is hereby incorporated by reference in its entirety. This arrangement uses four diverging beams emitted from a head unit. On movement of the user's head one of the beams may intersect a detector. The identity of the beam which insects the detector can be determined and the orientation of the user's head determined based on this information (with an endoscope being controlled as a result of this information). However, a need has arisen for alternative arrangements to be developed.

Other arrangements have been developed for detecting the orientation of, for example, an airplane pilot's head such that information displayed to the pilot can be altered accordingly. Arrangements also exist for controlling a view presented to a user in a virtual reality world based on a detected orientation of the user's head. These arrangements are, however, not suitable for use in a surgical environment. For example, in some cases these arrangements are bulky and expensive; in general there is a prejudice in the art against adapting such arrangements (which were developed for nonsurgical applications) for use in relation to a surgical mechanism or robot because of the perceived difficulties with sterilization, maintaining a sterile environment, excessive cost, limited space in an operating theatre, and meeting the strict safety regulations for equipment to be used in surgical operations.

It is an object of the present invention to seek to ameliorate some of the problems associated with the prior art.

Accordingly, one aspect of the present invention provides a surgical mechanism control system comprising: a beam emitter unit configured to emit only a single beam and adapted to be attached to a surgeon; a first pair of discrete beam detectors each adapted to detect an incident beam emitted by the beam emitter unit and output a corresponding control signal when in incident beam is detected; and a control unit configured to receive one or more control signals output by the beam detectors and control a surgical mechanism in accordance with the one or more control signals.

Preferably, the system further comprises a second pair of discrete beam detectors each adapted to detect an incident beam emitted by the beam emitter unit and output a corresponding control signal when in incident beam is detected.

Another aspect of the present invention provides a surgical mechanism control system comprising: a camera unit adapted to be attached to a surgeon and configured to capture an image frame; at least one marker detectable within an image frame captured by the camera; a processing unit configured to detect a position of the or each marker in an image frame captured by the camera and output a control signal in dependence on the position of the detected marker within the captured image frame; and a control unit configured to receive one or more control signals output by the processing unit and control a surgical mechanism in accordance with the one or more control signals.

Another aspect of the present invention provides a surgical mechanism control system comprising: a camera unit adapted to be attached to a surgeon and configured to capture an image frame; at least one marker detectable within an image frame captured by the camera; a processing unit configured to detect an identity of the or each marker in an image frame captured by the camera and output a control signal in dependence on the identity of the detected marker within the captured image frame; and a control unit configured to receive one or more control signals output by the processing unit and control a surgical mechanism in accordance with the one or more control signals.

Preferably, the or each marker is a physical marker.

Advantageously, the system further comprises a video overlay unit configured to superimpose a marker on a video signal.

Preferably, a plurality of markers are provided, each marker being substantially uniquely identifiable.

Another aspect of the present invention provides a surgical endoscopic tool positioning arrangement comprising: a laparoscope receiving module adapted to receive a laparoscope; at least one motor coupled to the laparoscope receiving module and configured to move the laparoscope receiving module when operated; a reflector configured to reflect electromagnetic radiation of a predetermined frequency and adapted to be attached to a surgeon; a detector unit adapted to monitor movement of the reflector by sensing the electromagnetic radiation reflected by the reflector; and a control unit configured to receive one or more control signals output by the detector unit and control the operation of the or each motor so as to control movement of the laparoscope receiving module in accordance with the one or more control signals.

Preferably, the arrangement further comprises two additional reflectors adapted to reflect electromagnetic radiation of respective substantially independent predetermined frequencies and adapted to be attached to a surgeon, wherein the detector unit is adapted to detect the frequency of electromagnetic radiation reflected by the reflectors and use this information to assist in monitoring the movement of the reflectors.

Another aspect of the present invention provides a surgical mechanism control system comprising: a beam emitter unit configured to emit two or more parallel beams, each beam being substantially uniquely identifiable, the beam emitter unit being adapted to be attached to a surgeon; a first beam detector adapted to detect two or more incident beams emitted by the beam emitter unit and output a corresponding control signal when a predetermined number of the two or more uniquely identifiable incident beams is detected; and a control unit configured to receive one or more control signals output by the beam detectors and control a surgical mechanism in accordance with the one or more control signals.

Another aspect of the present invention provides a surgical mechanism control system comprising: a beam emitter unit configured to emit only two divergent beams and adapted to be attached to a surgeon; a first pair of discrete elongate beam detectors each adapted to detect an incident beam emitted by the beam emitter unit and output a corresponding control signal when in incident beam is detected; and a control unit configured to receive one or more control signals output by the beam detectors and control a surgical mechanism in accordance with the one or more control signals.

Another aspect of the present invention provides a surgical location detection system comprising: two or more surgeon markers attachable to a surgeon; a stereoscopic detector adapted to detect movement of at least part of a surgeon based on a detected position of the two or more surgeon markers and output one or more control signals based on the detected movement; and a control unit configured to receive one or more control signals output by the stereoscopic detector and control a surgical mechanism in accordance with the one or more control signals.

Preferably, the system further comprises: a plurality of patient markers, wherein the stereoscopic detector is configured to detect the location of the patient markers and determine the location of the patient within a frame of reference of the system using the detected location of the patient markers.

Another aspect of the present invention provides a method of monitoring movement of a surgeon and providing control signals comprising: providing two or more surgeon markers attachable to a surgeon; attaching the two or more surgeon markers to the surgeon; providing a stereoscopic detector adapted to detect movement of at least part of a surgeon based on a detected position of the two or more surgeon markers and output one or more control signals based on the detected movement; and providing a control unit configured to receive one or more control signals output by the stereoscopic detector and control a surgical mechanism in accordance with the one or more control signals.

Another aspect of the present invention provides a surgical mechanism control system comprising: an acceleration or orientation detection unit configured output one or more control signals in response to detecting one of acceleration and orientation of the unit, the unit being adapted to be attached to a surgeon; and a control unit configured to receive one or more control signals output by the unit and control a surgical mechanism in accordance with the one or more control signals.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12 shows a component of an embodiment of the present invention.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
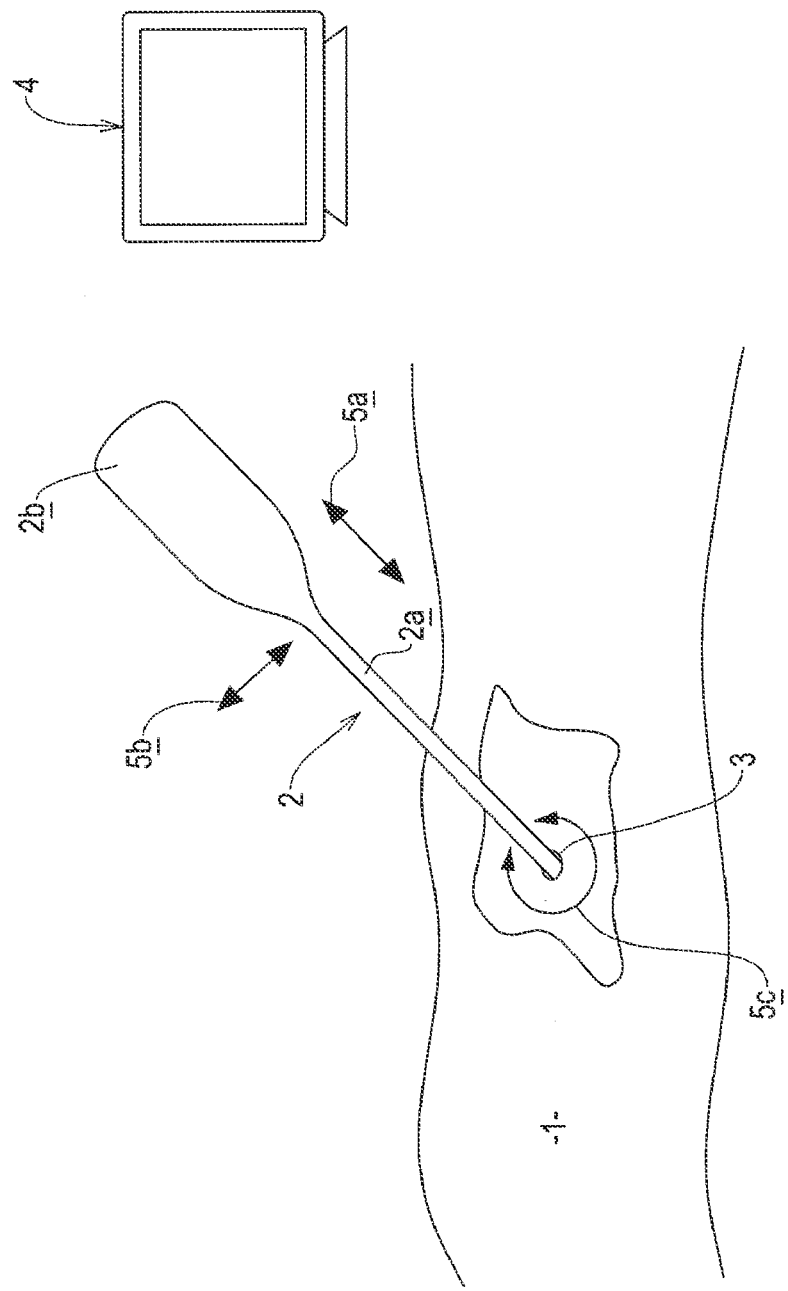
FIG. 1 shows an endoscope and a patient.

A patient 1 (draped in a sterile covering) is shown in FIG. 1. This figure also shows an endoscope 2 (which is, in this instance, a laparoscope) which has been passed through an incision 3 in the patient 1. The endoscope 2 comprises a shaft 2a and a camera 2b. The camera 2b is coupled to, for example, an optical fiber (not shown) running the length of the shaft 2a to a distal end of the endoscope 2 (i.e. the end of the endoscope 2 which is inside the patient and generally at a surgical site). A lens (not shown) may be provided at the distal end of the endoscope 2 generally covering an end of the optical fiber. An illumination means may also be provided at the distal end of the endoscope 2. An image of the surgical site at the distal end of the endoscope 2 is received through the optical fiber by the camera 2b. The image is transmitted from the camera 2b to a monitor 4 which displays the image for use by the surgeon.

An image of any relevant part of the surgical site can be obtained by moving the endoscope 2 such that the distal end of the endoscope 2 is in the desired location. It has been found that movements of the endoscope 2 in three degrees of freedom (centered on or intersecting the incision 3) provide a substantially complete range of possible endoscope 2 positions without risking excessive distortion of the incision 3 (which could cause injury to the patient). These three degrees of freedom of movement are indicated by double-headed arrows 5a, 5b, 5c in FIG. 1.

The first degree of freedom of movement 5a is generally in a direction which is parallel with a longitudinal axis of the endoscope 2. This is a zoom movement. The second degree of freedom of movement 5b is a tilt movement and the third degree of freedom of movement 5c is a pan movement (the pan and tilt movements being centered on the incision).

Figure 2:
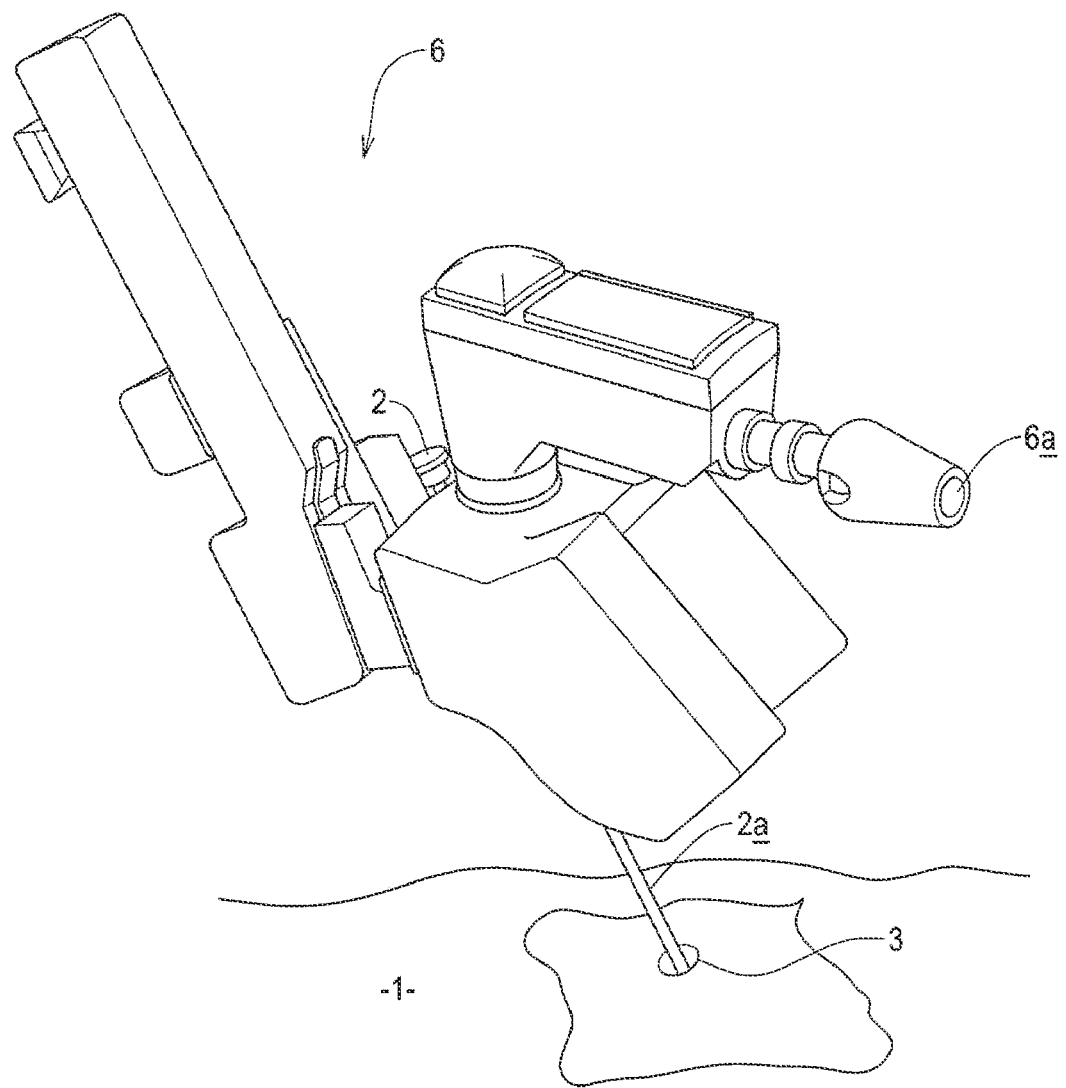
FIG. 2 shows a surgical endoscope positioning arrangement.

A surgical endoscope positioning arrangement 6 is shown in FIG. 2. The arrangement 6 can control movement of an endoscope 2 attached to the arrangement 6 in the manner described above (i.e. in three degrees of freedom of movement), is controllable by a surgeon, is easy to use, and is accurate and functional. It should be noted that the arrangement 6 is usually supported by a fixed arm (not shown) which is attached to the arrangement 6 at coupling unit 6a—this fixed arm has been omitted from FIG. 2 for the sake of clarity.

As discussed above the orientation arrangement disclosed in U.S. Pat. No. 6,239,874, which is hereby incorporated by reference in its entirety, is suitable for controlling the arrangement shown in FIG. 2. The arrangement disclosed in U.S. Pat. No. 6,239,874 can be adapted to use a foot pedal to change modes of operation to achieve control of movement in all three degrees of freedom of movement. There is a need for alternative orientation detection arrangements which are suitable to control a surgical arrangement such as the arrangement shown in FIG. 2.

As will be understood from the description presented below, the aim of embodiments of the present invention is to seek to provide a system which can generate control signals (preferably 6 different control signals) to control the movement of a surgical mechanism. The control signals are preferably generated by detecting movements of at least part of the body of a surgeon. This permits the surgeon to continue, for example, to hold endoscopic tools in place while contemporaneously controlling the position of an endoscope.

Figure 3:
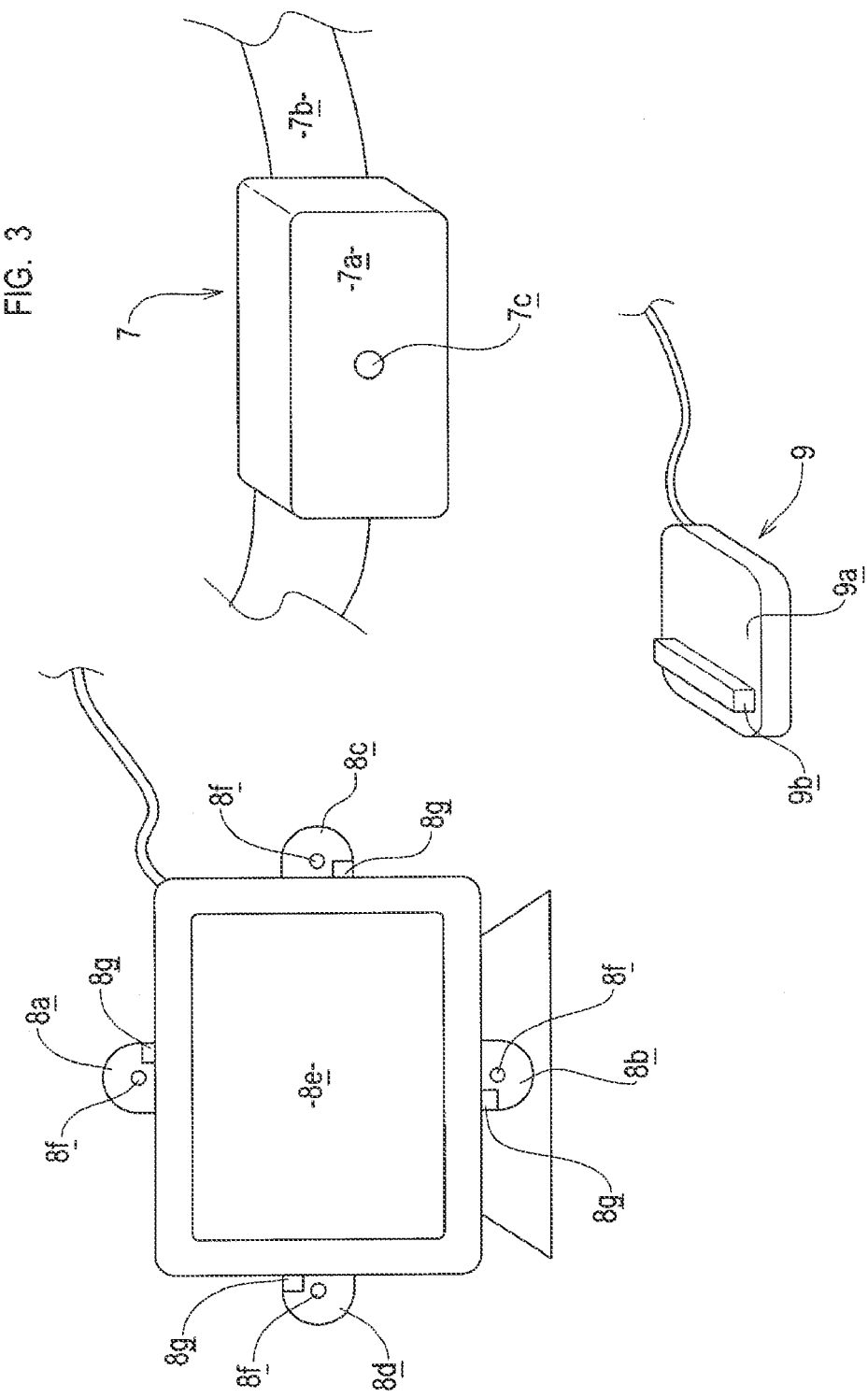
FIG. 3 shows components of an embodiment of the present invention.

Components of an embodiment of the present invention are shown in FIG. 3. The components include a head module 7 comprising a head unit 7a and a coupling arrangement 7b (in this case a strap) to secure the head module 7 to a user's head (in this case the user's forehead). The components also include four detection units 8a, 8b, 8c, 8d which are arranged around (and may be attached to) a monitor 8e, and a foot pedal 9 having a base section 9a and an actuation member 9b.

The detection units 8a, 8b, 8c, 8d may be positioned around the monitor 8e such that the detection units 8a, 8b, 8c, 8d comprise two pairs 8a, 8b and 8c, 8d of detectors—each pair of detectors comprising two detectors arranged opposite one another across a portion of the monitor 8e. The detectors 8a, 8b, 8c, 8d are discrete detectors—for example, the detectors do not comprise two different parts of a single CCD nor do they comprise an array of CCDs forming a single sensor.

The head unit 7a includes only a single beam emitter 7c which is generally aligned to emit a beam away from the head unit 7a. The emitter 7c is preferably an electromagnetic beam emitter (such as a light emitter) but may emit any form of detectable beam.

Each of the detector units 8a, 8b, 8c, 8d includes a beam detector 8f configured to detect the beam emitted by the single beam emitter 7c of the head unit 7a when that beam intersects the respective detector 8a, 8b, 8c, 8d.

Figure 4:
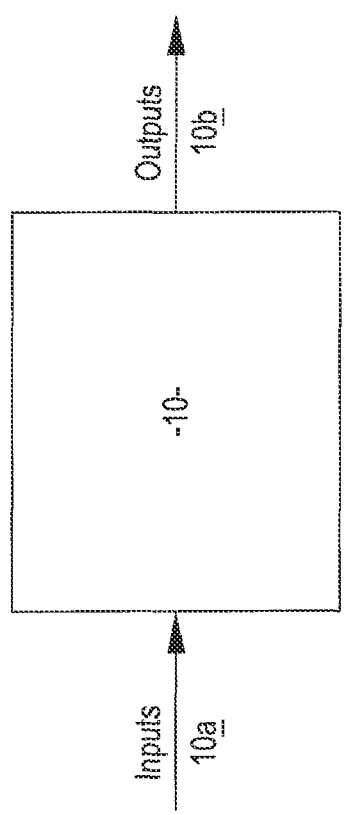
FIG. 4 shows a controller according to embodiments of the present invention.

The detector units 8a, 8b, 8c, 8d, each include a switch arrangement 8g which is actuated between an off-mode and an on-mode when the beam detector 8f of that unit 8a, 8b, 8c, 8d detects a beam emitted from the head unit 7a. The actuation of a switch unit 8g to an on-mode causes a corresponding control signal to be transmitted. In an embodiment, the control signal is transmitted to a controller 10 (see FIG. 4).

To prevent a user (e.g. a surgeon) causing inadvertent actuation of the switch units 8g, the foot pedal 9 may be used (as described below). An output (on/off) signal from the foot pedal is coupled to the controller 10.

The controller 10 receives an input 10a (for example from a detector 8a, 8b, 8c, 8d) and transmits an output 10b in accordance with the input 10a if an input 10a to the controller 10 from the foot pedal output is also detected (e.g. because a foot pedal actuation member 9b has been depressed with respect to a base section 9a of the foot pedal 9). The output 10b may be an actuation signal for part of a surgical endoscope positioning arrangement 6 (see FIG. 2). The actuation signal may provide power to a motor (not shown) in the surgical endoscope positioning arrangement 6 which drives movement of an attached endoscope 2 in one of the three degrees of freedom of movement as described above. In an embodiment the controller 10 comprises one or more electrical relays which are controlled by the control signals which may be transmitted by the detectors 8a, 8b, 8c, 8d and the output signal from the foot pedal 9 so as to close a power circuit for a motor of the surgical endoscope positioning arrangement 6 (two power circuits may be provided for each of three motors-one for each degree of freedom of movement). The controller 10 may be a control unit which does not perform any computation.

Alternatively, the foot pedal 9 may be coupled to the head unit 7a such that the beam emitter 7d only emits a beam when the foot pedal 9 is actuated. This means that the foot pedal 9 need not be coupled to the controller 10 and this has the potential to simplify the system.

The four detectors 8a, 8b, 8c, 8d provide four control signals. If it is desired to control, for example, the movement of a surgical endoscope positioning arrangement 6 in three degrees of freedom of movement (i.e. requiring a total of six control signals-one for each direction of movement in each degree of freedom of movement), then the foot pedal 9 can be used to determine a second mode of operation. For example, a quick tap on the foot pedal 9 may activate a second mode of operation which redirects one or more of the control signals transmitted to the controller 10 to a different part of the controller 10 (for example, a different relay). Thus, the same control signal or signals can be used to control a different output 10b from the controller 10 to control a different motor or power circuit of the surgical endoscope positioning arrangement 6.

The components of the embodiment of FIG. 3 provide a simple control mechanism which is easier and less expensive to construct than prior art arrangements for controlling a surgical endoscope positioning arrangement 6. For example, the above described head unit 7a uses just a single beam (as opposed to four beams). The detectors units 8a, 8b, 8c, 8d which are arranged around the monitor 8e are less prone to damage than a head unit and hence may have a longer operational life; as such, the provision of four detector units when compared to systems which use just one, is not, in this case, a detriment to the expense and reliability of the arrangement as a whole. The head unit 7a is lighter than the head unit 7a of the some prior art systems (because of the use of only a single beam emitter 7c). Indeed, the expense of the head unit 7a according to this embodiment may be sufficiently low that the head unit 7a can be provided as a single use item-thus avoiding expensive sterilization of the head unit 7a.

The head unit 7a may be provided in a substantially sealed blister pack (not shown). The coupling arrangement 7b may also be provided in the blister pack or may be provided separately and secured to the head unit 7a by means of a clip (not shown) of the head unit 7a.

Figure 5:
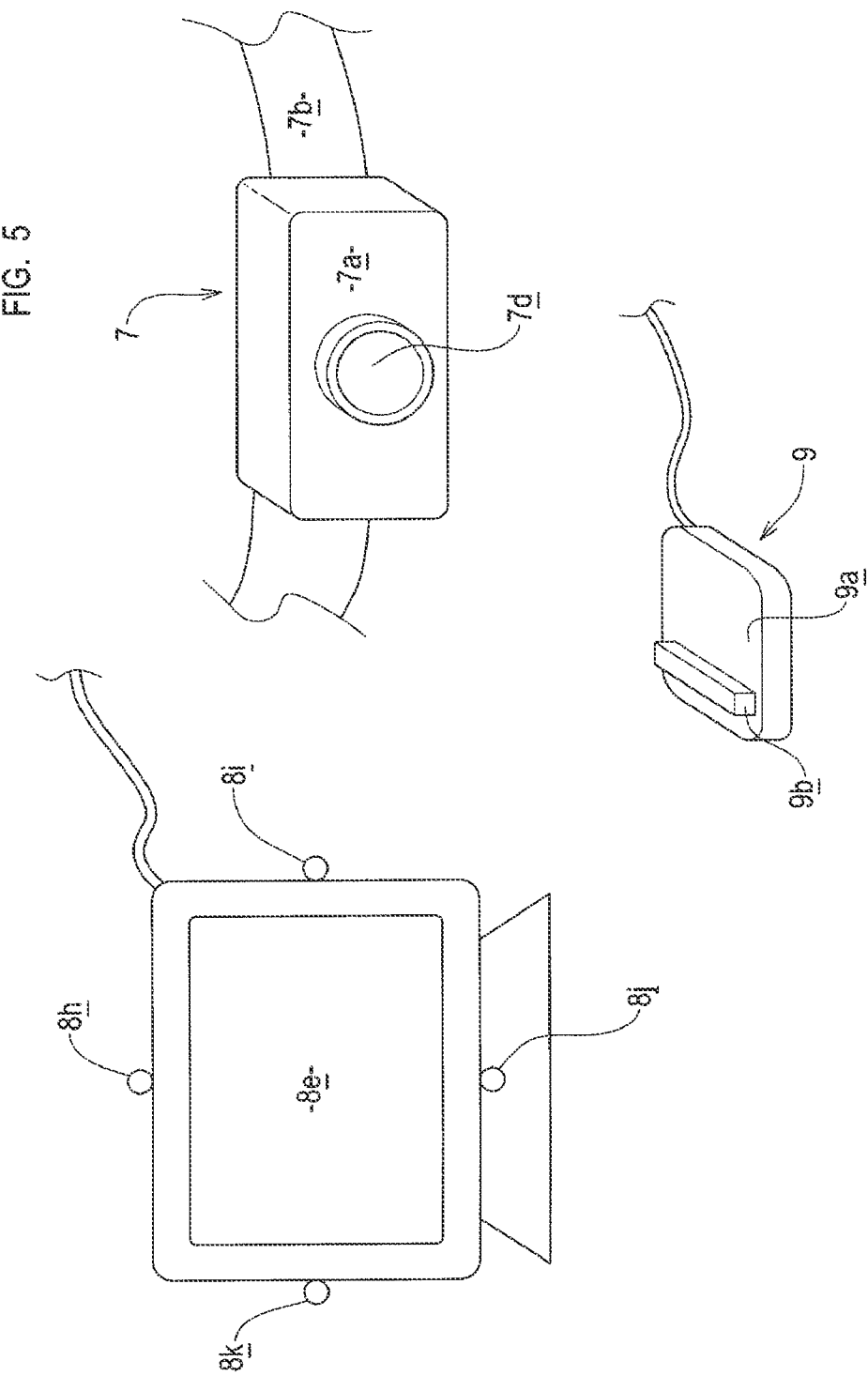
FIG. 5 shows components of an embodiment of the present invention.

Component parts of an embodiment of the present invention are shown in FIG. 5. Many of the component parts are similar to those shown in FIG. 3 and it will be understood that compatible features described in relation to FIG. 3 also apply to the embodiment shown in FIG. 5. To aid the reader's appreciation of the similarities between embodiments of the invention described herein, like reference numerals have been used for corresponding features in the various described embodiments.

In this embodiment, the head unit 7a includes a camera 7d. The camera 7d is preferably a digital camera based on a charged coupled device (CCD).

Instead of four detectors 8a, 8b, 8c, 8d, one or more markers 8h, 8i, 8j, 8k are provided and arranged relative to a monitor 8e.

The embodiment shown in its component form in FIG. 5 operates generally in the same way as the embodiment of FIG. 3 described above. However, instead of a detector 8a, 8b, 8c, 8d detecting an incident beam, in this embodiment, the camera 7d of the head unit 7a is configured to detect (or at least capture an image of) one or more of the one or more markers 8h, 8i, 8j, 8k which are arranged relative to the monitor 8e. The position of the one or more markers 8h, 8i, 8j, 8k within an image frame captured by the camera 7d of the head unit 7a permits the head unit 7a to determine the relative orientation of the head unit 7a or a control unit 10 coupled to the head unit 7a (and hence the user's head) with respect to the monitor 8e.

A single marker 8h, 8i, 8j, 8k could be used in this system to detect the relative orientation of the head unit 7a with respect of the monitor 8e. However, in an embodiment, four markers 8h, 8i, 8j, 8k are provided around the monitor 8e. One or more of these markers 8h, 8i, 8j, 8k are captured within an image frame of the camera 7d of the head unit 7a when the foot pedal 9 is actuated. If a single marker is used then the image frame captured by the camera 7d may be separated into a plurality of portions by a processing arrangement (not shown). The arrangement detects which of the plurality of portions include the marker and a control signal is output accordingly. If more than one marker is used, then the arrangement may detect a predetermined set of two or more of the portions which each contain a marker and issue a control signal accordingly.

Figure 6:
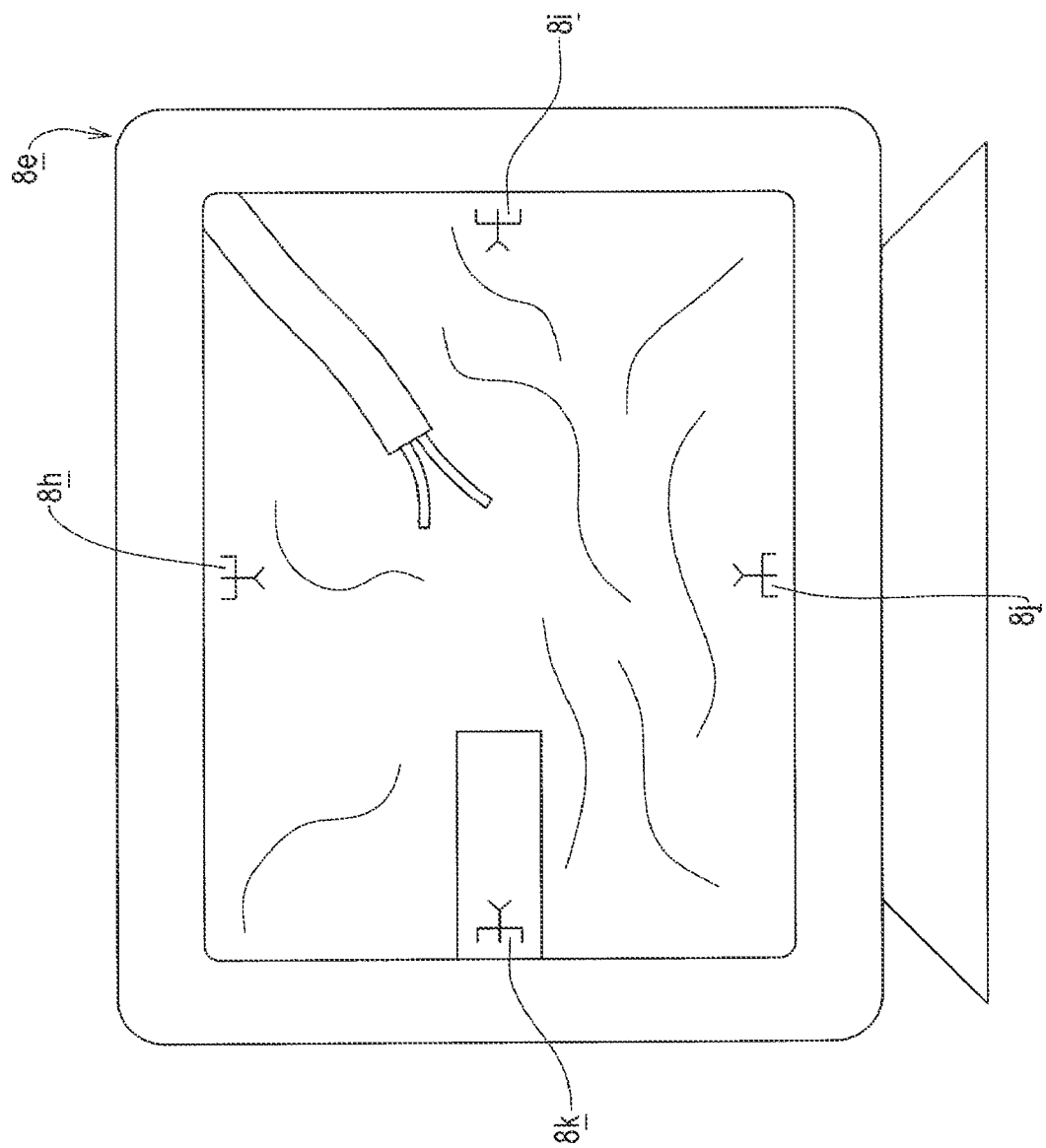
FIG. 6 shows a monitor according to an embodiment of the present invention.

As an alternative, instead of separate markers 8h, 8i, 8j, 8k, one or more symbols may be displayed on the monitor itself 8e. An example of this embodiment is shown in FIG. 6. In this example, the monitor 8e arranged to display an image of a surgical site along with parts of respective endoscopic tools. This is the image captured by the endoscope 2 for use by the surgeon. Four symbols 8h, 8i, 8j, 8k are superimposed on the image. This is preferably achieved electronically by altering the signal transmitted from the endoscope 2 to the monitor 8e. Instead of detecting the markers 8h, 8i, 8j, 8k, the camera 7d of the head unit 7a detects one or more of the symbols 8h, 8i, 8j, 8k. Control signals may be generated based on the position of one of these symbols 8h, 8i, 8j, 8k within the image frame captured by the camera 7d of the head unit 7a (as described above). Four such symbols 8h, 8i, 8j, 8k may be provided; each of the symbols is substantially unique in that it can be uniquely identified when compared to the other symbols. The image frame captured by the camera 7d may be sufficiently small so as to capture only a single symbol 8h, 8i, 8j, 8k. The head unit 7a may determine which of the four symbols 8h, 8i, 8j, 8k has been captured within the frame and hence will be able to determine the orientation of the surgeon's head and actuate control signals accordingly.

Figure 7:
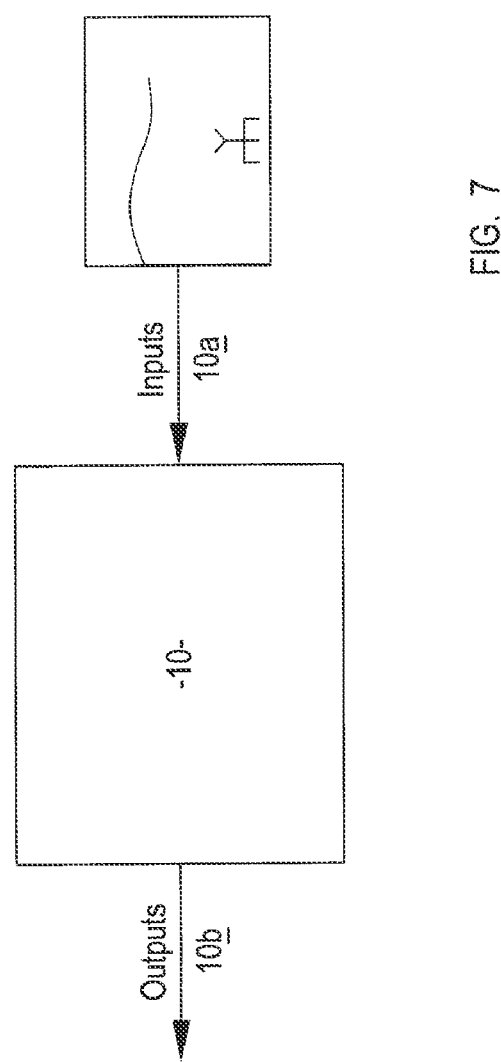
FIG. 7 shows a controller according to an embodiment of the present invention.

In an embodiment, the head unit 7a performs all of the processing steps described below. In an embodiment, the controller 10 performs some or all of the processing steps described below. The camera 7d of the head unit 7a simply captures an image and passes that image to the controller 10 which processes the captured image (as shown in FIG. 7) in order to determine, for example, which of the symbols has been captured. Of course, use of the controller 10 in this manner applies to the other embodiments described in relation to FIGS. 5 and 6.

It will be appreciated that the use of a camera 7d in this manner has several advantages over prior systems. For example, the image captured by the camera 7d may be separately stored for later use in, for example, training future surgeons or investigating the cause of an accident during an operation. Moreover, the system does not use the detectors used in the embodiment described above or in some of the prior systems. This greatly simplifies the operational set up. Indeed, as the symbols, in an embodiment, may be superimposed on the image displayed on the monitor 8e no additional equipment need be set up around the monitor 8e. Of course, in this embodiment, a unit (not shown) must be connected between the endoscope 2 and the monitor 8e so as to superimpose the image of the symbol or symbols.

Figure 8:
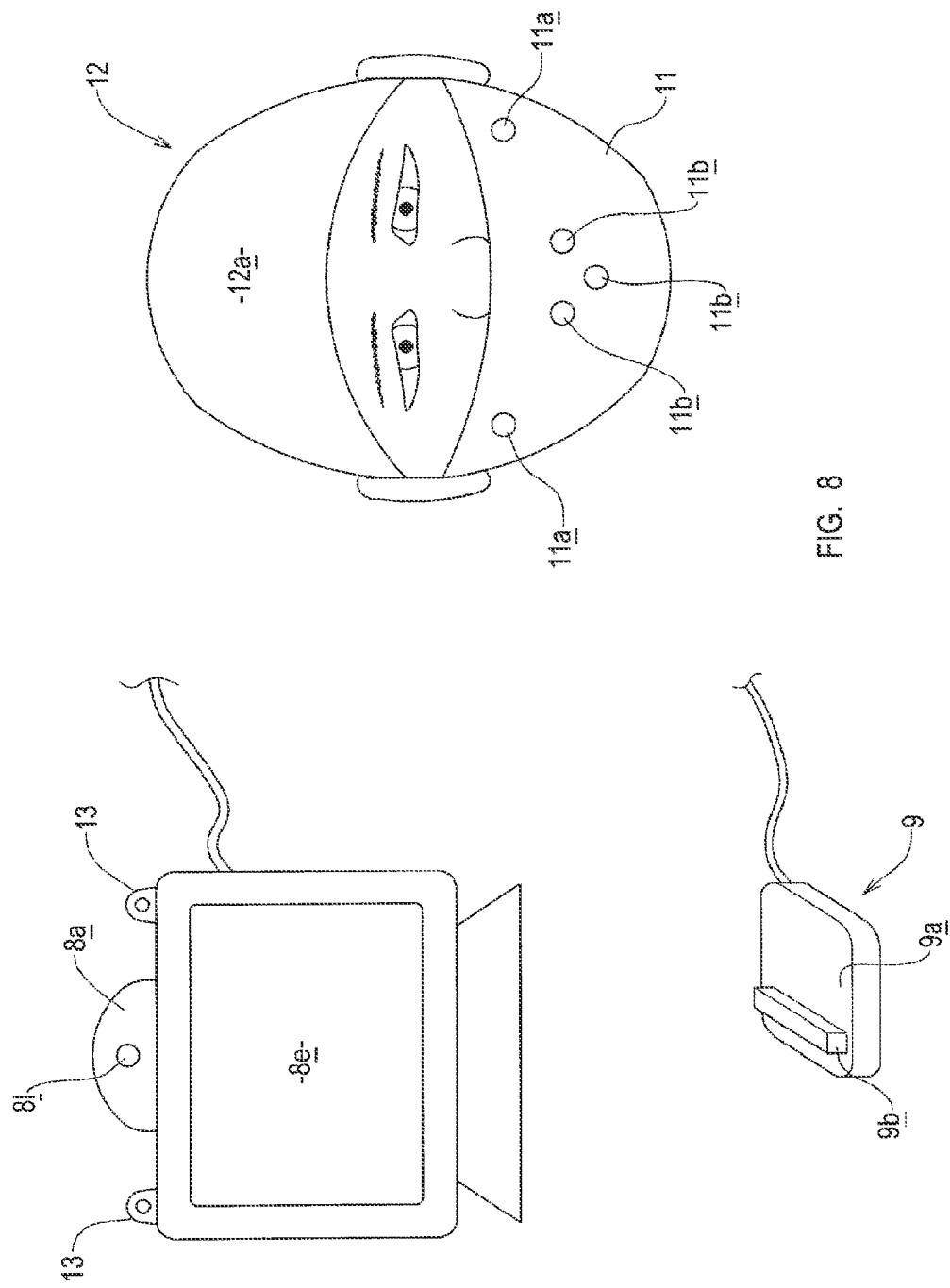
FIG. 8 shows components of an embodiment of the present invention.

Components for a further embodiment are shown in FIG. 8. In this embodiment a surgical mask 11 or other item of clothing (such as a head covering 12a) normally worn by a surgeon 12 in an operating theatre includes a number of reflective sections 11a, 11b. These reflective sections 11a, 11b may be grouped around the portion of the mask 11 which sits generally centrally on the face of the surgeon 12 when in use. Alternatively or in addition, one or more peripheral sections of the mask 11 may include reflective portions 11a.

As with previous embodiments, a monitor 8e is provided which displays the image captured by the endoscope 2. In this embodiment, a detector 8a is provided and arranged relative to the monitor 8e. The detector 8a includes a signal detector 8l. The signal detector 8l is preferably sensitive to specific frequencies of electromagnetic radiation (such as light of a particular frequency). The detector 8a is preferably sensitive to a frequency of electromagnetic radiation which corresponds with a section of the electromagnetic spectrum which the reflectors 11a, 11b are particularly efficient at reflecting (i.e. a detectable frequency).

One or more emitters 13 may be provided relative to the monitor 8e and configured to a emit electromagnetic radiation in the frequency range generally associated with the detectable frequency of the detector 8a.

The detector 8a, and specifically the signal detector 8l of the detector 8a, captures images of the surgeon 12 including the reflective sections 11a, 11b.

When a surgeon 12 wishes to control movement of the endoscope 2, the surgeon 12 may look directly at the monitor 8e (and hence the detector 8a) and depress the actuation member 9b of the foot pedal 9; the surgeon 12 may then rotate his head to the left or to the right up or down. Movement of the reflective sections 11a, 11b is monitored by the detector 8a or by the controller 10 coupled to the detector 8a based on the captured images; corresponding control signals are issued to the surgical endoscope positioning arrangement 6 in accordance with the detected movement.

In an embodiment, markers 11a which are not part of a central group of markers 11b, are adapted to reflect, to a greater extent, different frequencies of electromagnetic radiation. Thus, if at least one of each of these non-central markers 11a is located (when in use) on either side of a surgeon's face (or other body part if appropriate)—i.e. the markers 11a are on opposing ends of the mask 11—and each of these markers 11a reflects a different (potentially independent) frequency of electromagnetic radiation to a greater extent, then the detector 8a can use the detected frequency of radiation from the reflectors to determine or confirm which control signal to issue.

The advantages of this arrangement are apparent. For example, the surgical mask 11 worn by the surgeon 12 is entirely disposable and relatively cheap to produce. In addition, the surgical mask 11 is a piece of clothing which is already worn by the surgeon 12 during an operation. Hence, there is no additional clothing or equipment which must be worn by the surgeon 12 in order to use the system.

A surgeon may choose to wear a head covering 12a (or other equipment which may be worn by the surgeon in relation to other parts of the operation not connected with use of the described system may be used) carrying the reflective sections 11a, 11b instead of a surgical mask 11 depending on the surgeon's preference.

In an embodiment, the frequency of electromagnetic radiation used by the system is not within the visible range of light and hence has no effect on the surgeon's ability to see any part of the operating theatre.

Figure 9:
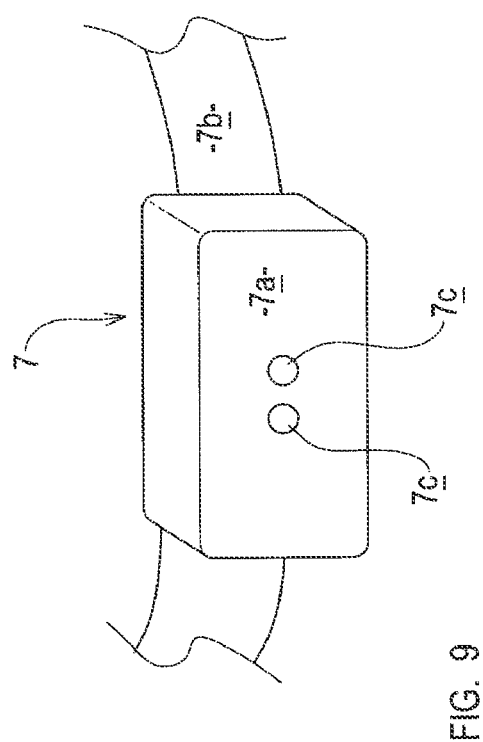
FIG. 9 shows a component of an embodiment of the present invention.

A head module 7 generally similar to the head module 7 described in relation to FIG. 3 above is shown in FIG. 9. This head module 7 includes two beam emitters which emit parallel beams. The two beams are each uniquely identifiable (for example, because they are each transmitted with a particular pulse code).

This head module 7 is used in relation to a similar monitor 8e and set of detectors 8a, 8b, 8c, 8d as described in relation to FIG. 3. However, in this embodiment, each detector 8a, 8b, 8c, 8d will only actuate its respective switch unit 8g if both of the two beams emitted by the two beam emitters 7c of the head unit 7a are detected.

The use of two parallel beams in this manner provides an added degree of safety and security and can be used to overcome certain interference problems.

In an alternative form of this embodiment, a pair of parallel beams could be used in the same manner in relation to an orientation detection arrangement substantially as described in U.S. Pat. No. 6,239,874 with the same advantages as discussed above.

More than two uniquely identifiable parallel beams could be used if necessary—for example three or more parallel beams could be used. The arrangement may be such that the switch unit 8g is actuated when a predetermined number of the parallel beams are detected. That predetermined number may not be all of the beams in a particular group of parallel beams (thus providing a degree of fault tolerance).

Figure 10:
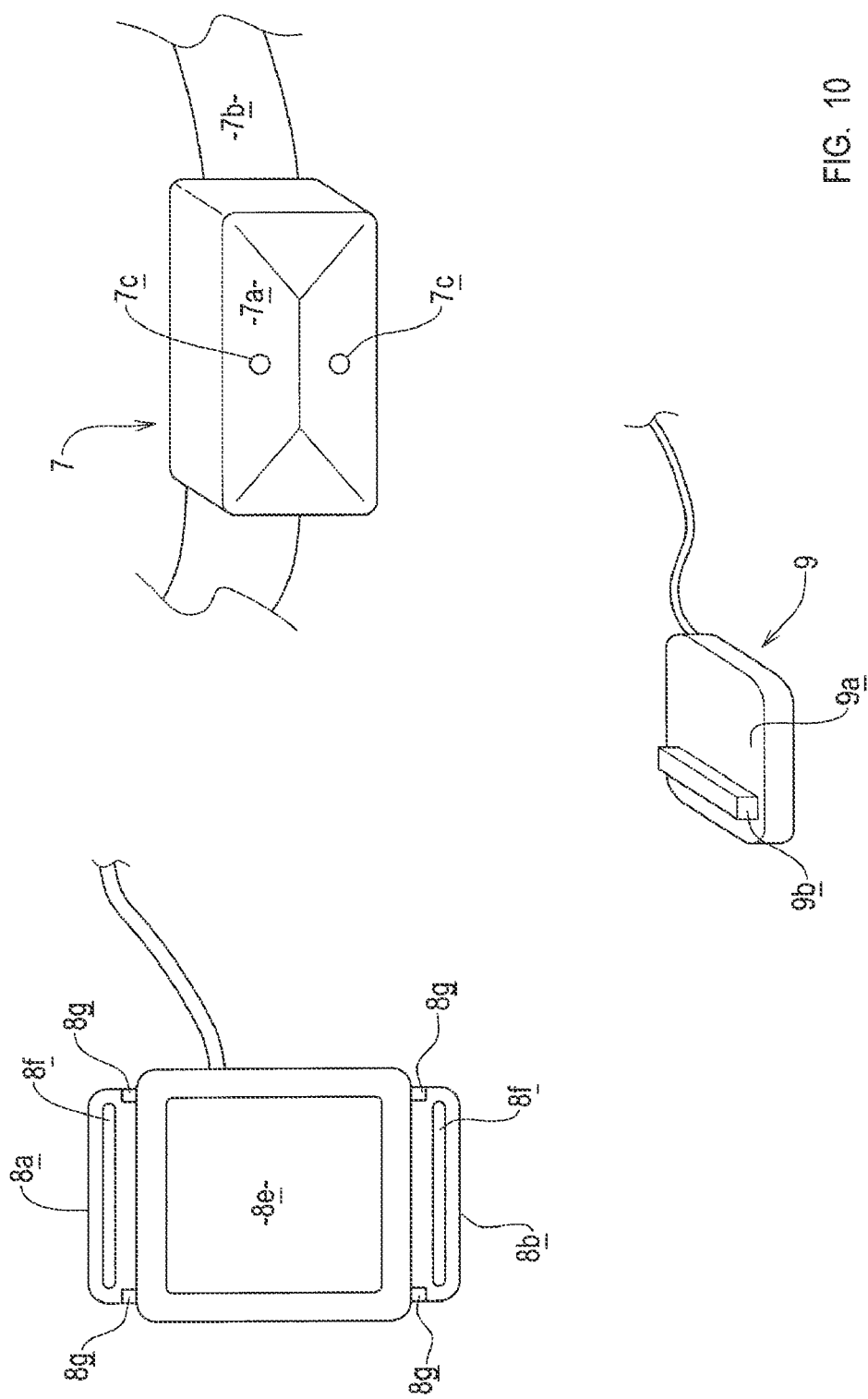
FIG. 10 shows components of an embodiment of the present invention.

Components of another embodiment are shown in FIG. 10. In this embodiment, ahead unit 7a includes only two beam emitters 7c which are configured to emit divergent beams.

Two elongate detectors 8a, 8b are provided and arranged relative to a monitor 8e such that one of the detectors 8a is adjacent the top of the monitor 8e and the other of the detectors 8b are adjacent the bottom of the monitor 8e.

The detectors 8a, 8b each comprise an elongate beam detector 8f which can detect an incident beam at any point along the length thereof and is provided with two switch units 8g. A first of the switch units 8g is actuated when an incident beam is detected towards a first end of detector 8f; a second of the switch units 8g is actuated when an incident beam is detected towards a second end of the detector 8f (which opposes the first end thereof); both switch units 8g are actuated if an incident beam is detected towards a middle portion of the beam detector 8f.

When the surgeon (wearing the head unit 7a) looks directly at the monitor 8e, the detectors 8a, 8b and beam emitters 7c are arranged such that beams emitted by the emitters 7c will each be incident with the middle portions of a respective one of the beam detectors 8f. All four of the switch units 8g (two for each detector 8a, 8b) are actuated and a control signal is sent to the controller 10. This control signal is a neutral control signal which does not result in movement of the surgical endoscope positioning arrangement 6, but may be used to initiate, for example, a power-up or warm-up process of the arrangement.

When the surgeon looks to the left or to the right then one of the switch units 8g of each of the detectors 8a, 8b will be actuated (as the beams are incident with one end of each beam detector 8f) and a relevant control signal transmitted (which results in a corresponding movement of an associated surgical endoscope positioning arrangement 6).

When the surgeon looks up or down, then both switch units 8g of one of the detectors 8a, 8b will actuate (as only one of the beams is incident with a detector 8a, 8b) and a relevant control signal is transmitted (which results in a corresponding movement of an associated surgical endoscope positioning arrangement 6).

The beams emitted by the head unit 7a may be substantially uniquely identifiable such that each detector 8a, 8b will be able to determine which of the two beams has been detected and may issue control signals accordingly. This adds an extra degree of safety should one of the beam emitters 7c fail (as this would otherwise cause the actuation of both of the switch units 8g of one of the detectors 8a, 8b and a corresponding, undesired, movement of the associated surgical endoscope positioning arrangement 6).

In an embodiment (not depicted), a single detector is provided relative to a monitor. In this embodiment, a head unit having two divergent beam emitters may be provided. The head unit and detector are arranged such that when a surgeon (wearing the head unit) is looking directly at the monitor, neither of the two divergent beams is incident with the detector.

The two beams emitted by the emitters of the head unit are substantially uniquely identifiable.

When the head unit (and hence the surgeon's head) is moved in one of a pair of opposing directions (e.g. up and down or left and right) then a respective beam will be detected and a first switch unit of the detector actuated (and a corresponding control signal transmitted). When the head unit is moved in a direction opposing this direction then the other beam will be detected and a second switch unit of the detector actuated (and a corresponding control signal transmitted). Thus, control of an associated surgical endoscope positioning arrangement in one degree of freedom of movement is possible. A different detector (see below) may be used to achieve control in a second degree of freedom of movement. A foot pedal may be used to achieve control in a third degree of freedom of movement (as discussed above) or in a second and third degree of freedom of movement with only on detector.

Figure 11:
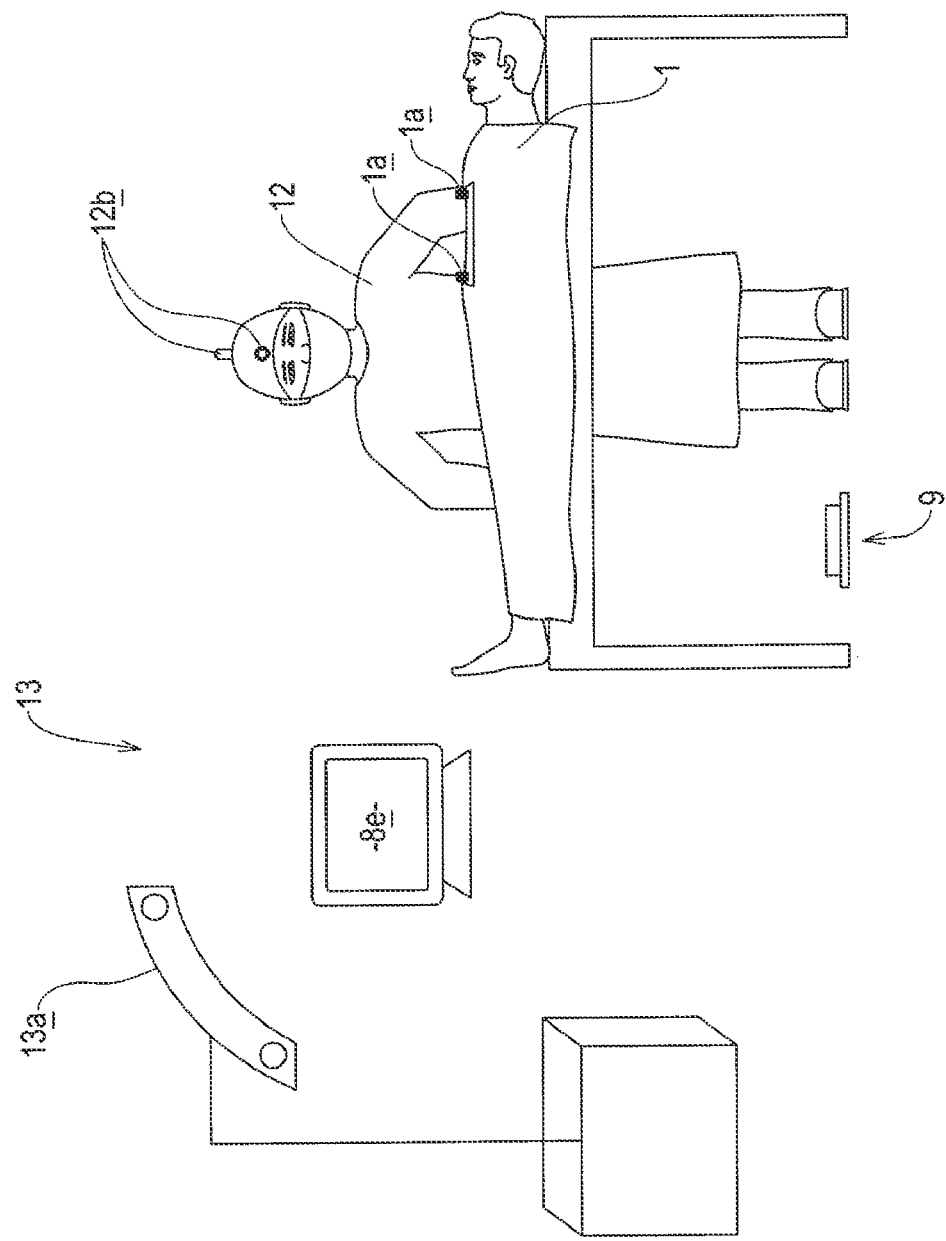
FIG. 11 shows components of an embodiment of the present invention.

As shown in FIG. 11, an operating theatre 13 may include an arrangement 13a configured to detect the location of one or more markers 1a on a patient 1. For example, one or more fiducial markers 1a may be secured to a patient 1 and used to register previously acquired images of the patient 1 (such as MR or CT images) with the current location of the patient 1 in the operating theatre 13 (i.e. in an operating theatre frame of reference-which may be a surgical robot frame of reference).

In this embodiment of the present invention, the same arrangement 13a which is used to detect the location of markers 1a attached to the patient 1 and register previously acquired images of the patient 1 within an operating theatre frame of reference is also used to detect the location of two or more markers 12b which are attached to, for example, the head of a surgeon 12.

A monitor 8e is provided as described above. The surgeon 12 initially uses the arrangement 13a to register the location of at least two markers 12b attached to part of the surgeon's body (such as his head). Subsequently, during an operation, movements of the at least two markers 12b are detected and these movements are converted into control signals for the associated surgical endoscope positioning arrangement 6 (not shown in FIG. 11).

Thus, the arrangement 13a performs two functions: registering pre-operative image of the patient with in an operating theatre frame of reference and providing control signals to the associated surgical endoscope positioning arrangement 6.

The precise location and orientation of the part of the surgeon 12 to which the markers 12b have been attached is not necessary; instead, it is sufficient that unique movements of that part of the surgeon 12 can be detected so that the correct control signals can be generated. As with other embodiments, the generation of control signals (and the detection of the movement of the surgeon 12) may only be detected on actuation of a foot pedal 9.

It will be appreciated that more than two markers 12b may be attached to part of the surgeon 12—for example, three or four markers may be used. The arrangement 13a may be configured to permit programming by a user such that user specific movements are used to generate control signals for the associated surgical endoscope positioning arrangement 6. Thus, a surgeon 12 may have a user profile stored in the arrangement 13a and containing information about what predefined movement will generate which control signal for the associated surgical endoscope positioning arrangement 6. Using this arrangement each surgeon 12 using a particular arrangement can have his own predetermined set of movements which cause corresponding movements of the associated surgical endoscope positioning arrangement 6.

A surgeon 12 may be required to perform calibration steps before each use of the system—for example, repeating the movements required to produce each control signal and confirming that the desired signal has been generated as a result of each movement.

The head unit 7a may include one or more acceleration sensors 14 (see FIG. 12). The or each acceleration sensor 14 may cause the actuation of an associated switch unit 14a. The acceleration sensors 14 may be Piezoelectric sensors. Preferably, the or each sensor 14 is configured to detect acceleration in a particular direction. A single sensor 14 may be used to detect acceleration in a pair of opposing directions.

Thus, the head unit 7a may be worn by a surgeon and an acceleration of the surgeon's head in a particular direction (e.g. up, down, left, or right) can be detected and a switch unit 14a actuated accordingly. The actuation of a switch unit 14a causes a control signal to be transmitted to a controller 10 such that an associated surgical endoscope positioning arrangement 6 is controlled in accordance with the detected movement of the head unit 7a.

Preferably, four acceleration sensors 14 are provided (one for detecting an upwards acceleration, one for detecting a downwards acceleration, one for detecting an acceleration to the right and one of detecting an acceleration to the left). As already mentioned, two acceleration sensors 14 may be used instead.

A foot pedal 9 may be used in relation to this embodiment as described in relation to other embodiments.

A detected acceleration in a particular direction causes a respective control signal to be transmitted. That control signal may cause the associated surgical endoscope positioning arrangement 6 to move in a particular direction until a second acceleration in a particular direction is detected and a further control signal transmitted. Alternatively, each detected acceleration of the head unit 7a may cause a step movement of the associated surgical endoscope positioning arrangement 6 a predetermined distance.

The acceleration sensors 14 preferably have an associated threshold acceleration. An acceleration below the threshold will not cause actuation of the associated switch unit 14a but an acceleration above the threshold will cause the associated switch unit 14a to actuate. Thus, a user can cause the transmission of a first control signal using a fast head movement (to control movement of the associated surgical endoscope positioning arrangement 6 in a first direction) and can then return their head to the original position without causing actuation of a second control signal (to control movement of the associated surgical endoscope positioning arrangement 6 in a second direction which is opposite to the first direction—for example). The use of a threshold also reduces the need for careful coordination between a head movement and actuation of a foot pedal 9 (if one is being used).

Systems have been developed to track movement of a user's eyes. This embodiment of the present invention (not depicted) uses such a system to control movement of a surgical endoscope positioning arrangement 6 in a similar manner to the arrangements described above but based on the detected movements of the surgeon's eyes.

In an embodiment, a head unit 7a includes an orientation detector (no shown). Such a detector may comprise a chamber (not shown) in which a pendulum (not shown) is located. The pendulum hangs freely with in the chamber. When a surgeon wearing the head unit 7a moves his head, the chamber will move with respect to the pendulum. The relative orientation of the pendulum to the rest of the chamber can be detected—for example by securing a conductor to a free end of the pendulum, the conductor being configured to contact an array of conducting rails disposed around an inner wall of the chamber to form an electrical circuit. By detecting which of the conducting rails is in electrical communication with the pendulum conductor, it is possible to determine the relative position of the pendulum within the chamber (if the positions of the conductive rails are known).

Similarly an orientation detector could comprise a chamber partially filled with a conductive fluid. An array of conductive rails are disposed around an internal surface of the chamber such that the orientation of a horizon determined by an upper surface of the liquid within the chamber can be determined. Thus, the surgeon may tilt his head backwards and forwards, left and right to cause respective actuation of four switch units in the head unit 7a by completing one of four or more different circuits using the conductive fluid.

It will be appreciated from the foregoing that the foot pedal 9 described specifically in relation to some embodiments may, in fact, be used in relation to all of the above embodiments. Actuation of the foot pedal 9 can be used to switch between modes of operation such that an arrangement which is otherwise only capable of issuing, for example, one or two control signals, can control movement of a surgical endoscope positioning arrangement 6 is more than one degree of freedom of movement.

The foot pedal 9 can also be used to activate an on and an off state or mode such that inadvertent movements by the surgeon do not cause corresponding movements of the arrangement 6.

It will be understood, that the controller 10 can play a greater or a lesser extent in the processing of control signals depending on the specific embodiment and the requirements of the system as a whole.

Various embodiments of the present invention permit combinational movements. In other words, the arrangements and systems of various of the embodiments described herein can be used to produce control signals which cause activation of more than one motor or power circuit in the surgical laparoscope positioning arrangement 6. Thus, embodiments of the present invention can cause movement in more than one of the degrees of freedom of movement of the arrangement at any one time (i.e. simultaneously). This may be achieved by permitting more than one control signal to be generated during a given period or by the provision of a library of pre-programmed movements. The correct programmed movement may be selected by a user moving in a specific combination of movements which are detected by the arrangements and systems discussed above.

It will also be understood, that various different combinations of the arrangements and systems described herein are possible. For example, two different systems and methods can be used in the same arrangement to cause movement of the surgical laparoscope positioning arrangement 6 in two different degrees of freedom of movement.

Although the term "head unit" and the like has been used frequently above, it will be clear that the unit may be attached to a different part of the body of a surgeon.

A system or arrangement embodying the present invention may use any combination of the component features as described above.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical mechanism control system comprising:
an acceleration or orientation detection unit configured to output one or more control signals in response to detecting one of acceleration and orientation of the unit, the unit being adapted to be attached to and carried by a surgeon, wherein the unit includes one or more acceleration sensors and wherein the or each acceleration sensor has an associated threshold acceleration, such that an acceleration below the associated threshold acceleration does not cause actuation of an associated switch unit of the acceleration or orientation detection unit and an acceleration above the associated threshold acceleration does cause the associated switch unit to actuate such that the one or more control signals are output; and
a control unit configured to receive the one or more control signals output by the acceleration or orientation detection unit and control a surgical mechanism in accordance with the one or more control signals, and
a foot pedal;
wherein the control unit is configured to transmit an output to the surgical mechanism in accordance with the one or more control signals when an input is detected at the control unit from the foot pedal.

2. The surgical mechanism control system according to claim 1, wherein the or each acceleration sensor is configured to detect acceleration in a particular direction.

3. The surgical mechanism control system according to claim 1, wherein the or each acceleration sensor is a Piezoelectric sensor.

4. The surgical mechanism control system according to claim 1, wherein a first of the one or more acceleration sensors is configured to detect acceleration in a pair of opposing directions.

5. The surgical mechanism control system according to claim 1, wherein there are four acceleration sensors, and wherein one of the acceleration sensors is configured for detecting an upwards acceleration, one of the acceleration sensors is configured for detecting a downwards acceleration, one of the acceleration sensors is configured for detecting an acceleration to the right and one of the acceleration sensors is configured for detecting an acceleration to the left.

6. The surgical mechanism control system according to claim 1, wherein the foot pedal is actuatable to switch between modes of operation, such that
   in a first mode of operation the one or more control signals control a first output from the control unit which controls movement of the surgical mechanism in a first degree of freedom, and
   in a second mode of operation the one or more control signal control a second output from the control unit which controls movement of the surgical mechanism in a second degree of freedom.

7. The surgical mechanism control system according to claim 1, wherein the associated threshold acceleration is a fixed threshold.

8. A surgical mechanism control system comprising:
   an acceleration or orientation detection unit configured to output one or more control signals in response to detecting one of acceleration and orientation of the unit, the unit being adapted to be attached to a surgeon, wherein the unit includes one or more acceleration sensors and wherein the or each acceleration sensor has an associated threshold acceleration, such that an acceleration below the associated threshold acceleration does not cause actuation of an associated switch unit and an acceleration above the associated threshold acceleration does cause the associated switch unit to actuate such that the one or more control signals are output; and
   a control unit configured to receive the one or more control signals output by the acceleration or orientation detection unit and control a surgical mechanism in accordance with the one or more control signals, and
   a foot pedal;
   wherein the foot pedal is actuatable to switch between modes of operation, such that
   in a first mode of operation the one or more control signals control a first output from the control unit which controls movement of the surgical mechanism in a first degree of freedom, and
   in a second mode of operation the one or more control signal control a second output from the control unit which controls movement of the surgical mechanism in a second degree of freedom.

9. The surgical mechanism control system according to claim 8, wherein the control unit is configured to transmit an output to the surgical mechanism in accordance with the one or more control signals when an input is detected at the control unit from the foot pedal.

10. The surgical mechanism control system according to claim 8, wherein the or each acceleration sensor is configured to detect acceleration in a particular direction.

11. The surgical mechanism control system according to claim 8, wherein the or each acceleration sensor is a Piezoelectric sensor.

12. The surgical mechanism control system according to claim 8, wherein a first of the one or more acceleration sensors is configured to detect acceleration in a pair of opposing directions.

13. The surgical mechanism control system according to claim 8, wherein there are four acceleration sensors, and wherein one of the acceleration sensors is configured for detecting an upwards acceleration, one of the acceleration sensors is configured for detecting a downwards acceleration, one of the acceleration sensors is configured for detecting an acceleration to the right and one of the acceleration sensors is configured for detecting an acceleration to the left.

* * * * *